US012663369B2

(12) United States Patent (10) Patent No.: US 12,663,369 B2
Li et al. (45) Date of Patent: Jun. 23, 2026

(54) CEEMDAN-BASED METHOD FOR SCREENING AND MONITORING SOIL MOISTURE STRESS IN AGRICULTURAL FIELDS

(71) Applicants: North China Institute of Aerospace Engineering, Langfang (CN); Aerospace informaiton Research Institute, Chinese Academy of Sciences, Beijing (CN)

(72) Inventors: Xuqing Li, Langfang (CN); Yongtao Jin, Langfang (CN); Xiaodan Wang, Langfang (CN); Guohong Li, Langfang (CN); Xingfa Gu, Langfang (CN); Yuanping Liu, Langfang (CN); Xia Zhu, Langfang (CN); Qichao Zhao, Langfang (CN); Yuyan Liu, Langfang (CN); Xiufeng Yang, Langfang (CN); Yancang Wang, Langfang (CN); Tianjiao Liu, Langfang (CN); Wenhao Zhang, Langfang (CN); Chenyu Zhao, Langfang (CN)

(73) Assignee: North China Institute of Aerospace Engineering, Langfang (CN)

( * ) Notice: Subject to any disclaimer, the term of this patent is extended or adjusted under 35 U.S.C. 154(b) by 489 days.

(21) Appl. No.: 18/143,849

(22) Filed: May 5, 2023

(65) Prior Publication Data

US 2024/0167947 A1 May 23, 2024

Related U.S. Application Data

(63) Continuation of application No. PCT/CN2023/078316, filed on Feb. 27, 2023.

(30) Foreign Application Priority Data

Nov. 10, 2022 (CN) .......................... 202211402702.3

(51) Int. Cl.
*G01N 21/359* (2014.01)
*G01N 21/3563* (2014.01)
(Continued)

(52) U.S. Cl.
CPC ....... *G01N 21/359* (2013.01); *G01N 21/3563* (2013.01); *G01N 33/0098* (2013.01); *G01N 33/24* (2013.01); *G01N 33/245* (2024.05)

(58) Field of Classification Search
CPC ............. G01N 21/359; G01N 21/3563; G01N 33/0098; G01N 33/24; G01N 33/245
See application file for complete search history.

(56) References Cited

FOREIGN PATENT DOCUMENTS

CN 110322032 A * 10/2019 ............. G06Q 40/04
CN 113111799 A * 7/2021 ......... G06F 18/2135
(Continued)

OTHER PUBLICATIONS

CN-113111799-A, Li, Xu-Quing , Jul. 13, 2021, pp. 1-25 (Year: 2021).*
(Continued)

*Primary Examiner* — Michael J Dalbo
*Assistant Examiner* — Kaleria Knox
(74) *Attorney, Agent, or Firm* — JEEN IP LAW, LLC

(57) ABSTRACT

The present invention discloses a CEEMDAN-based method for screening and monitoring soil moisture stress in farmland, characterised by the steps: preprocessing of remote sensing images, construction of NDVI long time series, CEEMDAN decomposition, calculation of statistical descriptors, screening of soil moisture stress sequences, ground data measurement, construction of soil moisture stress characteristic curves, fitting of soil moisture stress response characteristic curves and predicting the content of soil moisture stress. The invention adopts CEEMDAN decomposition, which solves the problems of noise residue (Continued)

preprocessing of remote sensing images
↓
construction of NDVI long time series
↓
CEEMDAN decomposition
↓
calculation of statistical descriptors
↓
screening of soil moisture stress sequences
↓
ground data measurement
↓
construction of soil moisture stress characteristic curves
↓
fitting of soil moisture stress response characteristic curves
↓
predicting the content of soil moisture stress and low reconstruction accuracy in the previous methods, and the high reconstruction accuracy of decomposed component data is more conducive to capturing the transient effects of soil moisture stress, and realizes the screening and extraction of soil moisture stress by combining with the ground measured data. The inverse model of soil moisture content is fitted by combining the effects of multiple indicators, and the CEEMDAN algorithm with remote sensing technology tools to achieve accurate monitoring of soil moisture in a large area of farmland.

5 Claims, 2 Drawing Sheets

(51) Int. Cl.
 *G01N 33/00*          (2006.01)
 *G01N 33/24*          (2006.01)

(56)               References Cited

FOREIGN PATENT DOCUMENTS

| CN | 114676636 | A | * | 6/2022 | ............... | G06N 3/04 |
| CN | 115661601 | A | * | 1/2023 | ........... | G01N 21/359 |

OTHER PUBLICATIONS

CN-115661601-A, Li, Xu-Quing , Mar. 31, 2023, pp. 1-13 (Year: 2023).*
CN-114676636-A, 2022-06-28, Wei, Dan-dan, pp. 1-18 (Year: 2022).*
CN-110322032-A, Lee-Zhi, Oct. 11, 2019, pp. 1-7 (Year: 2019).*

* cited by examiner

CEEMDAN-BASED METHOD FOR SCREENING AND MONITORING SOIL MOISTURE STRESS IN AGRICULTURAL FIELDS

BACKGROUND OF THE INVENTION

Field of the Invention

The present invention relates to a CEEMDAN-based method for screening and monitoring soil moisture stress in agricultural fields and belongs to the field of remote sensing technology.

Description of the Related Art

Traditional methods of measuring soil moisture content include contact and indirect methods, such as time domain reflectometry and capacitive sensors, and indirect methods such as passive microwave radiometers and scatterometers. Conventional methods can measure the soil moisture content in real time, but they are only suitable for small scales on the experimental site. The traditional methods are time consuming and difficult to use for large scale measurements and are not suitable for monitoring large areas. Remote sensing technology has developed rapidly in recent years, and the speed of remote sensing data collection and the high frequency of information updates fully demonstrate its significant advantages in dynamic real-time monitoring of large areas. Among them, optical remote sensing methods have the advantage of high spatial resolution, and optical vegetation index data is highly correlated with soil moisture and is one of the most commonly used data for soil moisture monitoring. The Chinese-made GF-1 satellite has broken through key technologies such as high temporal resolution, multi-spectral and wide coverage combination of optical remote sensing, with 16 meters resolution multi-spectral band images and a short revisit cycle, reaching the leading level of domestic and international civil optical remote sensing satellites in terms of comprehensive indicators of resolution and width, and has been widely used in related research. Normalized difference vegetation index (NDVI) is defined as the difference in reflectance between the near infrared band and the red band divided by the sum of reflectance between the near infrared band and the red band and is one of the most important parameters for crop growth. The NDVI enhances the response to vegetation by eliminating most of the variation in irradiance associated with instrument calibration, solar angle, topography, cloud shadow and atmospheric conditions.

The complexity of the growing environment of crops in natural farmland ecosystems leads to the influence of multiple stress factors such as soil moisture stress, soil heavy metal stress and soil fertility stress, which are interactive and concomitant. The long time series of vegetation indices extracted from remote sensing imagery are characterised by multiple sources and complexity, overlapping multiple time scales, non-linearity and non-smoothness. Processing is required to achieve the extraction of specific features, in particular signal processing methods with an adaptive approach to decompose the vegetation index sequence and extract the components characterising the specific features. Accurate screening and extraction of soil moisture stress and the removal of other stresses such as soil heavy metal stress and soil fertility stress during crop growth are key to accurate soil moisture monitoring in agricultural fields. The ensemble empirical mode decomposition (EEMD) algorithm improves on the empirical mode decomposition (EMD) algorithm by continuously decomposing the original long time series data to obtain the intrinsic mode function (IMF) component, which is eventually decomposed into a number of single frequency sequences and a residual component form. Some scholars decomposed the month-by-month precipitation data by EEMD algorithm and established a statistical forecasting model to realize the monthly forecast of summer precipitation in the middle and upper reaches of the Yellow River region. Another scholar proposed a rice heavy metal stress identification model based on spatial and temporal feature indicators to realize the monitoring of rice heavy metal stress. Some scholars screened the characteristics of rice heavy metal stress signals based on EEMD algorithm, and the extraction results could better reflect the response of stress signals to rice heavy metal stress. Previous methods have demonstrated the feasibility of using long time series data for stress screening and the advantages of the EEMD algorithm for extracting feature quantities at different time scales, but there are still several shortcomings and deficiencies. Firstly, the monitoring of soil moisture is mostly based on precipitation or drought and flood data, and the advantages of remote sensing vegetation index data are not fully utilized. The decomposition and extraction of remote sensing vegetation index data are mostly for long-term stress information with stability, such as heavy metals, but the soil moisture stress, which is a component of short-term stress, cannot be accurately identified and extracted. In addition, although the EEMD algorithm can extract feature quantities at different time scales, noise will still remain in its decomposed IMF, affecting the subsequent processing and analysis of the feature components, resulting in poor final monitoring accuracy.

The complete ensemble empirical mode decomposition with adaptive noise (CEEMDAN) algorithm decomposes long time series, which can well solve the noise transfer and residual problems, and provides a new idea for soil moisture stress screening and monitoring in agricultural fields.

SUMMARY OF THE INVENTION

The purpose of the present invention is to provide a method for screening and monitoring soil moisture stress in agricultural fields based on CEEMDAN.

To solve the above technical problems, the technical solutions used in the present invention are as follows.

A CEEMDAN-based method for screening and monitoring soil moisture stress in agricultural fields, comprising the steps as follows.

Step 1: Preprocessing of remote sensing images. Radiometric calibration, atmospheric correction and geometric correction pre-processed on all N remote sensing images.

Step 2: Construction of NDVI long time series. Calculation of NDVI long time series x(n), $1 \leq n \leq N$ based on pre-processed remote sensing image data.

$$x(n) = \frac{\rho_{NIR}(n) - \rho_{RED}(n)}{\rho_{NIR}(n) + \rho_{RED}(n)} \qquad \text{(formula 1)}$$

In formula 1, $\rho_{NIR}(n)$ is the reflectance of the nth remote sensing image in the near infrared band and $\rho_{RED}(n)$ is the reflectance of the nth remote sensing image in the red band to construct a long time series of NDVI for crops in natural farmland ecosystems.

Step 3: CEEMDAN decomposition. The NDVI long time series is decomposed based on CEEMDAN algorithm. The decomposition process is as follows.

First add adaptive white noise $Z^{(m)}(n)$ to the NDVI long time series $x(n)$, where m denotes the number of times the noise is added, $1 \leq m \leq 50$, to obtain the first signal to be decomposed:

$$x_1^{(m)}(n) = x(n) + \varepsilon_m Z^{(m)}(n)$$

$\varepsilon_m$ is the standard deviation of the mth addition of white noise, the first IMF component obtained from the CEEMDAN decomposition is as follows.

$$IMF_1 = \frac{1}{50} \sum_{m=1}^{50} IMF_1^{(m)}$$

$$IMF_1^{(m)}$$

denotes the IMF component obtained by EMD decomposition of the first signal $$x_1^{(m)}(n)$$

to be decomposed. The first residual term is $S_1(n)=x(n)-IMG_1$.

The rth to-be-decomposed signal $$x_r^{(m)}(n) = S_{r-1}(n) + \varepsilon_m Z^{(m)}(n)$$

is obtained by superimposing white noise on the (r−1)th residual term, and the rth to-be-decomposed signal $$x_r^{(m)}(n)$$

is decomposed again by EMD to obtain the IMF component $$IMF_r^{(m)}.$$

The rth IMF component is then as follows.

$$IMF_r = \frac{1}{50} \sum_{m=1}^{50} IMF_r^{(m)}$$

The rth residual term is $S_r(n)=S_{r-1}(n)-IMF_r$, r−1, . . . , R.

Step 4: Calculation of statistical descriptors. Calculating statistical descriptors for the first to Rth IMF component IMF,r−1, . . . , R, the statistical descriptors including period of fluctuation ($P_r$), mean ($M_r$), variance ($V_r$), variance contribution margin ($C_r$) and pearson correlation coefficient ($PS_r$), where $K_r$ is the number of extreme value points of the rth eigenmodal component $IMF_r$, r−1, . . . , R.

$$P_r = \frac{N}{K_r} \tag{formula 2}$$

$$M_r = \frac{1}{N} \sum_{n=1}^{N} IMF_r(n) \tag{formula 3}$$

$$V_r = \frac{1}{N} \sum_{n=1}^{N} \left( IMF_r(n) - \frac{1}{N} \sum_{n=1}^{N} IMF_r(n) \right)^2 \tag{formula 4}$$

$$C_r = \frac{\sum_{n=1}^{N} \left( IMF_r(n) - \frac{1}{N} \sum_{n=1}^{N} IMF_r(n) \right)^2}{\sum_{n=1}^{N} \left( x(n) - \frac{1}{N} \sum_{n=1}^{N} x(n) \right)^2} \tag{formula 5}$$

$$PS_r = \frac{\sum_{n=1}^{N} \left( IMF_r(n) - \frac{1}{N} \sum_{n=1}^{N} IMF_r(n) \right)\left( x(n) - \frac{1}{N} \sum_{n=1}^{N} x(n) \right)}{\sqrt{\sum_{n=1}^{N} \left( IMF_r(n) - \frac{1}{N} \sum_{n=1}^{N} IMF_r(n) \right)^2 \sum_{n=1}^{N} \left( x(n) - \frac{1}{N} \sum_{n=1}^{N} x(n) \right)^2}} \tag{formula 6}$$

$$C_r = \frac{\sum_{n=1}^{N} \left( IMF_r(n) - \frac{1}{N} \sum_{n=1}^{N} IMF_r(n) \right)^2}{\sum_{n=1}^{N} \left( x(n) - \frac{1}{N} \sum_{n=1}^{N} x(n) \right)^2} \tag{formula 5}$$

$$PS_r = \frac{\sum_{n=1}^{N} \left( IMF_r(n) - \frac{1}{N} \sum_{n=1}^{N} IMF_r(n) \right)\left( x(n) - \frac{1}{N} \sum_{n=1}^{N} x(n) \right)}{\sqrt{\sum_{n=1}^{N} \left( IMF_r(n) - \frac{1}{N} \sum_{n=1}^{N} IMF_r(n) \right)^2 \sum_{n=1}^{N} \left( x(n) - \frac{1}{N} \sum_{n=1}^{N} x(n) \right)^2}} \tag{formula 6}$$

Step 5: Screening of soil moisture stress sequences. Soil moisture stress sequences are identified by combining the statistical descriptors described above with the mechanistic characteristics of soil moisture stress. IMF components that meet the characteristics of short-period soil moisture stress and the identification conditions are summed and synthesized into soil moisture stress sequences.

Step 6: Ground data measurement. Chlorophyll content of crop leaves is determined using a hand-held chlorophyll meter by weighing the fresh biomass of the crop plant (FB), using the drying method at a predetermined killing temperature for a predetermined time, turning the temperature to a predetermined drying temperature and drying to a constant weight, then weighing its dry biomass (DB) and calculating the plant water content (PWC).

$$PWC = \frac{FB - DB}{FB} \times 100\% \tag{formula 7}$$

Weigh the wet weight of the soil sample (FW), dry it to a constant weight using the drying method at a preset drying temperature, then weigh its dry weight (DW) and calculate the soil moisture content (SMC).

$$SMC = \frac{FW - DW}{DW} \times 100\% \qquad \text{(formula 8)}$$

Step 7: Construction of soil moisture stress characteristic curves. Take the two points n and n+1 of the soil moisture stress sequence including the measured time t and the corresponding values y(n) and y(n+1), and fit the corresponding value of the measured time t as the corresponding soil moisture stress content Y(t) at the measured time point.

$$Y(t)=(t-n)(y(n+1)-y(n))+y(n) \qquad \text{(formula 9)}$$

Step 8: Fitting of soil moisture stress response characteristic curves. Soil moisture stress content is used as the independent variable and chlorophyll content is used as the dependent variable to construct the chlorophyll response index. Soil moisture stress is used as the independent variable and plant water content is used as the dependent variable to construct the wheat moisture content response index; the function of soil moisture stress and chlorophyll content and the function of soil moisture stress and plant water content are fitted.

Step 9: Predicting the content of soil moisture stress. Constructe the model to predict the degree of soil moisture stress by inverting the soil moisture content between three indicators, soil moisture stress, chlorophyll response to soil moisture stress and wheat moisture content response to soil moisture stress.

Further, the conditions for screening soil moisture stress sequences in step 5 are that the fluctuation period $P_r$ is less than 7, the mean value $M_r$ is the smallest, and the variance $V_r$, variance contribution $C_r$ and pearson correlation coefficient $PS_r$ are the largest.

Further, screening out soil moisture stress sequences in step 5 and synthesizes the first and second IMF components $IMF_1$ and $IMF_2$ cumulatively into a soil moisture stress sequence.

$$y(n) = \sum_{n=1}^{N} (IMF_1(n) + IMF_2(n)) \qquad \text{(formula 10)}$$

Further, the quadratic curve is used to fit chlorophyll content as a function of soil moisture stress and a composite curve is used to fit wheat moisture content as a function of soil moisture stress in step 8.

Further, the chlorophyll content as a function of the amount of soil moisture stress content in step 8 described is $y=58.241-19.917x-393.742x^2$ and the plant water content as a function of the amount of soil moisture stress content is $y=68.121+0.404^2$.

And finally, the model between soil moisture stress, chlorophyll response to soil moisture stress and wheat moisture response to soil moisture stress and soil moisture content in step 9 is as follows.

$$SMC=20.58-0.02x_1+10^{-2}x_2-1.76x_3-2\times10^{-3}x_1x_2-0.065x_1x_3-0.045x_2x_3-1.83\times10^{-4}x_1^2+7.91\times10^{-5}x_2^2+3.99x_3^2$$

$x_1$ represents chlorophyll response to soil moisture stress, $x_2$ represents wheat moisture response to soil moisture stress and $x_3$ represents soil moisture stress content.

With the above technical solutions, the beneficial effects of the invention are as follows.

1. The invention combines the CEEMDAN algorithm with remote sensing technology to achieve accurate monitoring of soil moisture in large areas of agricultural land and to improve the accuracy of the inversion.

2. The CEEMDAN algorithm is used for decomposition, which has better completeness and solves the noise transfer and residual problems of traditional algorithms. It not only solves the modal mixing problem and noise transfer problem, but also improves the adaptiveness of the algorithm and the reconstruction accuracy of the component data.

3. The invention constructs a fitting function between multiple indicators and soil moisture content, covering the multifaceted influence of multivariate indicators on soil moisture content, to achieve accurate monitoring of soil moisture content.

BRIEF DESCRIPTION OF THE DRAWINGS

The invention is described in further detail below in conjunction with the attached drawings and specific embodiments.

DETAILED DESCRIPTION

Example 1

Figure 1:
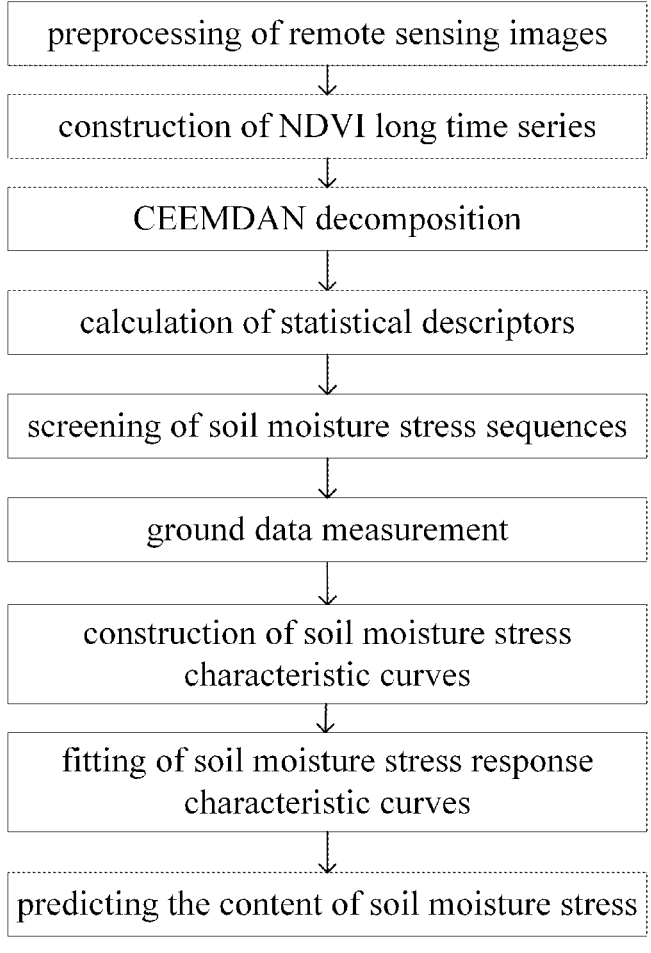
FIG. 1 is the flow chart of the invention.
Figure 2:
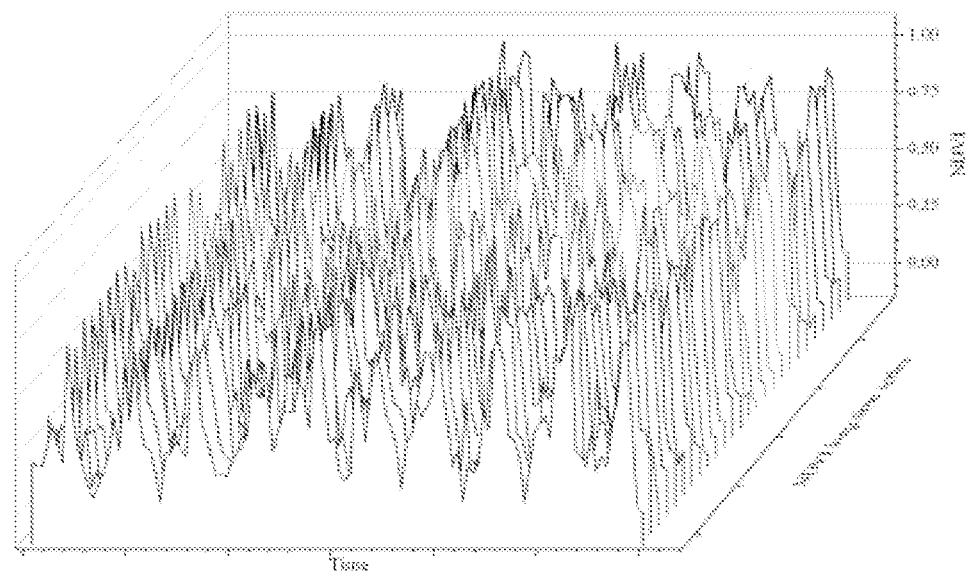
FIG. 2 is a NDVI long time series diagram in example 2 of the invention.

A CEEMDAN-based method for screening and monitoring soil moisture stress in agricultural fields, comprising the steps as follows.

Step 1: Preprocessing of remote sensing images. Radiometric calibration, atmospheric correction and geometric correction pre-processed on all N remote sensing images.

Step 2: Construction of NDVI long time series. Calculation of NDVI long time series x(n), $1 \leq n \leq N$ based on pre-processed remote sensing image data.

$$x(n) = \frac{\rho_{NIR(n)} - \rho_{RED(n)}}{\rho_{NIR(n)} + \rho_{RED(n)}} \qquad \text{(formula 1)}$$

In formula 1, $\rho_{NIR}(n)$ is the reflectance of the nth remote sensing image in the near infrared band and $\rho_{RED}(n)$ is the reflectance of the nth remote sensing image in the red band to construct a long time series of NDVI for crops in natural farmland ecosystems.

Step 3: CEEMDAN decomposition. The NDVI long time series is decomposed based on CEEMDAN algorithm. The decomposition process is as follows.

First add adaptive white noise $Z^{(m)}(n)$ to the NDVI long time series x(n) where m indicates the number of times the noise is added, generally take 10 to 50, this example take 50, then the NDVI long time series signal after the mth adaptive white noise is added for the first time can be expressed as follows.

$$x_1^{(m)}(n) = x(n) + \varepsilon_m Z^{(m)}(n)$$

$\varepsilon_m$ is the standard deviation of the mth addition of white noise and m takes values from 1 to 50, the first IMF component obtained from the CEEMDAN decomposition is as follows.

$$IMF_1 = \frac{1}{50}\sum_{m=1}^{50} IMF_1^{(m)}$$

$$IMF_1^{(m)}$$

denotes the IMF component obtained by EMD decomposition of the first signal $$x_1^{(m)}(n)$$

to be decomposed. The first residual term is $S_1(n)=x(n)-IMF_1$. The new signa $$x_2^{(m)}(n) = S_1(n) + \varepsilon_m Z^{(m)}(n)$$

to be decomposed is obtained by superimposing white noise on the first residual term, and the new signal $$x_2^{(m)}(n)$$

to be decomposed is again subjected to EMD decomposition to obtain the IMF component, the second component $$IMF_2^{(m)}$$

obtained by CEEMDAN decomposition is as follows.

$$IMF_2 = \frac{1}{50}\sum_{m=1}^{50} IMF_2^{(m)}$$

The second residual term is $S_2(n)=S_1(n)-IMF_2$. Repeat the above process to obtain the first to Rth IMF components $IMF_r$, r=1, . . . , R, with the final residual term $S_R=S_{R-1}(n)-IMF_R$.

Step 4: Calculation of statistical descriptors. Calculating statistical descriptors for the first to Rth IMF component $IMF_r$, r-1, . . . , R. The statistical descriptors including period of fluctuation ($P_r$), mean ($M_r$), variance ($V_r$), variance contribution margin ($C_r$) and pearson correlation coefficient ($PS_r$), where $K_r$ is the number of extreme value points of the rth eigenmodal component $IMF_r$, r=1, . . . , R.

$$P_r = \frac{N}{K_r} \qquad \text{(formula 2)}$$

$$M_r = \frac{1}{N}\sum_{n=1}^{N} IMF_r(n) \qquad \text{(formula 3)}$$

$$V_r = \frac{1}{N}\sum_{n=1}^{N}\left(IMF_r(n) - \frac{1}{N}\sum_{n=1}^{N} IMF_r(n)\right)^2 \qquad \text{(formula 4)}$$

-continued $$C_r = \frac{\sum_{n=1}^{N}\left(IMF_r(n) - \frac{1}{N}\sum_{n=1}^{N} IMF_r(n)\right)^2}{\sum_{n=1}^{N}\left(x(n) - \frac{1}{N}\sum_{n=1}^{N} x(n)\right)^2} \qquad \text{(formula 5)}$$

$$PS_r = \qquad \text{(formula 6)}$$

$$\frac{\sum_{n=1}^{N}\left(IMF_r(n) - \frac{1}{N}\sum_{n=1}^{N} IMF_r(n)\right)\left(x(n) - \frac{1}{N}\sum_{n=1}^{N} x(n)\right)}{\sqrt{\sum_{n=1}^{N}\left(IMF_r(n) - \frac{1}{N}\sum_{n=1}^{N} IMF_r(n)\right)^2 \sum_{n=1}^{N}\left(x(n) - \frac{1}{N}\sum_{n=1}^{N} x(n)\right)^2}}$$

Step 5: Screening of soil moisture stress sequences. Soil moisture stress sequences are identified by combining the statistical descriptors described above with the mechanistic characteristics of soil moisture stress. Soil moisture stress subsequences are screened on the condition that the fluctuation period $P_r$ is less than 7, the mean value $M_r$ is the smallest, and the variance $V_r$, variance contribution $C_r$ and pearson correlation coefficient $PS_r$ are the largest. The first and second IMF components $IMF_1$ and $IMF_2$ met the short-period soil moisture stress characteristics and screening conditions, and the first and second IMF components $IMF_1$ and $IMF_2$ are summed to form the soil moisture stress sequence as follows.

$$y(n) = \sum_{n=1}^{N}(IMF_1(n) + IMF_2(n)) \qquad \text{(formula 7)}$$

Step 6: Ground data measurement. Chlorophyll content of crop leaves is determined using a hand-held chlorophyll meter, avoiding the leaf veins and nearby locations of the plant leaves when measuring. The intact plants are dug up using a sapper and brought back to the laboratory in a sealed bag, the roots are cleaned of impurities and dried with absorbent paper, the fresh biomass is weighed on a balance with 0.1 g accuracy and the fresh biomass (FB) is measured using the drying method at 105° C. for two hours, then the temperature is turned down to 80° C. and dried to a constant weight and the dry biomass (DB) is weighed and the plant water content (PWC) is calculated. The soil within 5 to 10 centimeter of the sample point is sealed and brought back to the laboratory. The wet weight (FW) of the soil sample is weighed with a balance of 0.1 g accuracy, the soil sample is dried to a constant weight in an oven at 105° C., then its dry weight (DW) is weighed, and finally the soil moisture content (SMC) is calculated.

$$PWC = \frac{FB - DB}{FB} \times 100\% \qquad \text{(formula 8)}$$

$$SMC = \frac{FW - DW}{DW} \times 100\% \qquad \text{(formula 9)}$$

Step 7: Construction of soil moisture stress characteristic curves. Take the two points n and n+1 of the soil moisture stress sequence including the measured time t and the corresponding values y(n) and y(n+1), and fit the corresponding value of the measured time t as the corresponding soil moisture stress content Y(t) at the measured time point.

$$Y(t)=(t-n)(y(n-1)-y(n))+y(n) \qquad \text{(formula 10)}$$

Step 8: Fitting of soil moisture stress response characteristic curves. Soil moisture stress content is used as the independent variable and chlorophyll content is used as the dependent variable to construct the chlorophyll response index. Soil moisture stress is used as the independent variable and plant water content is used as the dependent variable to construct the wheat moisture content response index; the function of soil moisture stress and chlorophyll content and the function of soil moisture stress and plant water content are fitted.

Step 9: Predicting the content of soil moisture stress. Constructe the model to predict the degree of soil moisture stress by inverting the soil moisture content between three indicators, soil moisture stress, chlorophyll response to soil moisture stress and wheat moisture content response to soil moisture stress.

$$SMC=20.58-0.02x_1+10^{-2}x_2-1.76x_3-2\times10^{-3}x_1x_2-0.065x_1x_3-0.045x_2x_3-1.83\times10^{-4}x_1{}^2+7.91\times10^{-5}x_2{}^2+3.99x_3{}^2$$

$x_1$ represents chlorophyll response to soil moisture stress, $x_2$ represents wheat moisture response to soil moisture stress and $x_3$ represents soil moisture stress content.

This example uses a quadratic curve to fit the chlorophyll content as a function of soil moisture stress and a composite curve to fit the plant water content as a function of soil moisture stress. The relationship between chlorophyll content and soil moisture stress is $y=58.241-19.917x-393.742^2$, while the relationship between plant water content and soil moisture stress is $y=68.121+0.404^x$. The fitting results show that the chlorophyll response to soil moisture stress index and the wheat moisture response ti soil moisture stress index can effectively reflect the chlorophyll content and plant water content in response to soil moisture stress.

finally build a multi-indicator inversion model for accurate monitoring of soil moisture content.

The reconstruction accuracy of this example using CEEMDAN decomposition reached 100%, indicating that the summation of each IMF component after decomposition can obtain the nature of the original data. CEEMDAN decomposition only produces a unique IMF residual term, effectively solving the problem of transferring white noise from high to low frequencies, fully demonstrating the completeness of data reconstruction and reflecting the advantages of CEEMDAN decomposition. CEEMDAN reduces the interference of white noise on the original data and retains the detailed information of the original data. The use of CEEMDAN algorithm can better capture the transient effects of soil moisture stress belonging to short-term stress components, which is conducive to the accurate screening and extraction of soil moisture stress and the subsequent improvement of soil moisture content inversion accuracy.

When crops are stressed by soil moisture, there is a high reflectance in the visible band and a low reflectance in the near infrared band, resulting in a significant decrease in NDVI values. Soil moisture stress is a short-term stress with a short fluctuation period, the short duration of the stress means that the components characterising short-term stress are more correlated with the original data than those characterising long-term stress. The first and second IMF components $IMF_1$ and $IMF_2$ are identified as soil moisture stress subsequence because they had the lowest mean, the highest variance and variance contribution, and the highest pearson correlation coefficient with the original data, with a fluctuation period of less than 7 months (winter wheat growth cycle). The first to and second IMF components $IMF_1$ and $IMF_2$ are synthesised to characterise the effect of soil moisture stress on winter wheat during the growth cycle. Table 1 provides a statistical description of each IMF for this example.

TABLE 1

| IMF | fluctuation period | mean | variance | variance contribution | pearson correlation coefficient |
|-----|-------------------|------|----------|----------------------|-------------------------------|
| $IMF_1$ | 1.600000 | −0.010651 | 0.013138 | 0.322034 | 0.606323 |
| $IMF_2$ | 4.285714 | −0.007224 | 0.019400 | 0.475524 | 0.693123 |
| $IMF_3$ | 8.000000 | 0.001574 | 0.006527 | 0.159974 | 0.304420 |
| $IMF_4$ | 13.333333 | −0.001395 | 0.001710 | 0.041914 | 0.133364 |
| $IMF_5$ | 20.000000 | −0.003233 | 0.000453 | 0.011113 | 0.196660 |
| $IMF_6$ | 60.000000 | 0.391738 | 0.000052 | 0.001282 | 0.228038 |

The NDVI long time series are constructed based on the remote sensing images of GF-1. The long time series are decomposed by CEEMDAN to obtain each IMF component, and the statistical descriptive indexes such as fluctuation period, mean, variance, variance contribution and pearson correlation coefficient are calculated for each component. The ground data are measured at different fertility stages of crops, and the chlorophyll content of plant leaves, plant water content and soil moisture content are measured to obtain the real values of ground indicators in natural agroecosystems. The IMF components are compared and analysed to extract the soil moisture stress subsequence, and then the soil moisture stress subsequences are synthesised to obtain the soil moisture stress sequence. Combining the soil moisture stress data with the ground measured data, we construct the chlorophyll response index and the wheat moisture content response index for soil moisture stress, and

The invention claimed is:

1. A CEEMDAN-based method for screening and monitoring soil moisture stress in agricultural fields, where the CEEMDAN refers to a algorithm of complete ensemble empirical mode decomposition with adaptive noise, comprising the steps as follows:

Step 1: preprocessing radiometric calibration, atmospheric correction and geometric correction on all N remote sensing images;

Step 2: calculating of NDVI long time series x(n), $1 \leq n \leq N$ based on pre-processed remote sensing image data:

$$x(n) = \frac{\rho_{NIR(n)} - \rho_{RED(n)}}{\rho_{NIR(n)} + \rho_{RED(n)}} \qquad \text{(formula 1)}$$

in formula 1, $\rho_{NIR}(n)$ is a reflectance of a nth remote sensing image in a near infrared band and $\rho_{RED}(n)$ is the reflectance of the nth remote sensing image in a red band to construct a long time series of NDVI for crops in natural farmland ecosystems;

Step 3: decomposing the NDVI long time series based on CEEMDAN algorithm, a decomposition process thereof is as follows:

first add adaptive white noise $Z^{(m)}(n)$ to the NDVI long time series x(n), where m denotes the number of times the noise is added, $1 \leq m \leq 50$, to obtain the first signal to be decomposed:

$$x_1^{(m)}(n) = x(n) + \varepsilon_m Z^{(m)}(n)$$

$\varepsilon_m$ is a standard deviation of a mth addition of white noise, a first IMF component obtained from the CEEMDAN decomposition is as follows:

$$IMF_1 = \frac{1}{50}\sum_{m=1}^{50} IMF_1^{(m)}$$

$$IMF_1^{(m)}$$

denotes a IMF component obtained by EMD decomposition of the first signal $$x_1^{(m)}(n)$$

to be decomposed, and the first residual term is $s_1(n)=x(n)-IMF_1$;

a rth to-be-decomposed signal $$x_r^{(m)}(n) = S_{r-1}(n) + \varepsilon_m Z^{(m)}(n)$$

is obtained by superimposing white noise on the (r−1)th residual term, and the rth to-be-decomposed signal $$x_r^{(m)}(n)$$

is decomposed again by EMD to obtain a IMF component $$IMF_r^{(m)},$$

and the rth IMF component is then as follows:

$$IMF_r = \frac{1}{50}\sum_{m=1}^{50} IMF_r^{(m)}$$

a rth residual term is $S_r(n)=S_{r-1}(n)-IMF_r$, r=1, . . . , R;

Step 4: calculating statistical descriptors for the first to Rth IMF component $IMF_r$, r=1, . . . , R, the statistical descriptors including period of fluctuation ($P_r$), mean ($M_r$), variance ($V_r$), variance contribution margin ($C_r$) and pearson correlation coefficient ($PS_r$), where $K_r$ is the number of extreme value points of the rth eigen-modal component $IMF_r$, r=1, . . . , R;

$$P_r = \frac{N}{K_r} \quad \text{(formula 2)}$$

$$M_r = \frac{1}{N}\sum_{n=1}^{N} IMF_r(n) \quad \text{(formula 3)}$$

$$V_r = \frac{1}{N}\sum_{n=1}^{N}\left(IMF_r(n) - \frac{1}{N}\sum_{n=1}^{N}IMF_r(n)\right)^2 \quad \text{(formula 4)}$$

$$C_r = \frac{\sum_{n=1}^{N}\left(IMF_r(n) - \frac{1}{N}\sum_{n=1}^{N}IMF_r(n)\right)^2}{\sum_{n=1}^{N}\left(x(n) - \frac{1}{N}\sum_{n=1}^{N}x(n)\right)^2} \quad \text{(formula 5)}$$

$$\text{(formula 6)}$$

$$PS_r = $$

$$\frac{\sum_{n=1}^{N}\left(IMF_r(n) - \frac{1}{N}\sum_{n=1}^{N}IMF_r(n)\right)\left(x(n) - \frac{1}{N}\sum_{n=1}^{N}x(n)\right)}{\sqrt{\sum_{n=1}^{N}\left(IMF_r(n) - \frac{1}{N}\sum_{n=1}^{N}IMF_r(n)\right)^2 \sum_{n=1}^{N}\left(x(n) - \frac{1}{N}\sum_{n=1}^{N}x(n)\right)^2}}$$

Step 5: screening of soil moisture stress sequences, wherein the soil moisture stress sequences are identified by combining the statistical descriptors described above with mechanistic characteristics of soil moisture stress, IMF components that meet characteristics of short-period soil moisture stress and identification conditions are summed and synthesized into the soil moisture stress sequences;

Step 6: determining Chlorophyll content of crop leaves through a hand-held chlorophyll meter by weighing a fresh biomass of a crop plant (FB), using a drying method at a predetermined killing temperature for a predetermined time, turning the temperature to a pre-determined drying temperature and drying to a constant weight, then weighing its dry biomass (DB) and cal-culating a plant water content (PWC);

$$PWC = \frac{FB - DB}{FB} \times 100\% \quad \text{(formula 7)}$$

weighing the wet weight of the soil sample (FW), drying the soil sample to a constant weight using the drying method at a preset drying temperature, then weighing its dry weight (DW) and calculating a soil moisture content (SMC);

$$SMC = \frac{FW - DW}{DW} \times 100\% \quad \text{(formula 8)}$$

Step 7: constructing of soil moisture stress characteristic curves by taking two points n and n+1 of the soil moisture stress sequence including the measured time t and corresponding values y(n) and y(n+1), and fitting the corresponding value of the measured time t as the corresponding soil moisture stress content Y(t) at the measured time point;

$$Y(t)=(t-n)(y(n+1)-y(n))+y(n) \qquad \text{(formula 9)}$$

Step 8: fitting of soil moisture stress response characteristic curves, where the moisture stress content is used as the independent variable and chlorophyll content is used as the dependent variable to construct a chlorophyll response index; the soil moisture stress is used as the independent variable and plant water content is used as the dependent variable to construct a wheat moisture content response index; the function of soil moisture stress and chlorophyll content and the function of soil moisture stress and plant water content are fitted; wherein a quadratic curve is used to fit chlorophyll content as a function of soil moisture stress and a composite curve is used to fit wheat moisture content as a function of soil moisture stress;

Step 9: predicting the content of soil moisture stress, where the model is constructed to predict the degree of soil moisture stress by inverting the soil moisture content between three indicators, soil moisture stress, chlorophyll response to soil moisture stress and wheat moisture content response to soil moisture stress.

2. The method for screening and monitoring soil moisture stress in agricultural fields based on CEEMDAN according to claim 1, characterized in that the conditions for screening soil moisture stress sequences in step 5 are that the fluctuation period $P_r$ is less than 7, the mean value $M_r$ is the smallest, and the variance $V_r$, variance contribution $C_r$ and pearson correlation coefficient $PS_r$ are the largest.

3. The method for screening and monitoring soil moisture stress in agricultural fields based on CEEMDAN according to claim 2, characterized in that the model between soil moisture stress, chlorophyll response to soil moisture stress and wheat moisture response to soil moisture stress and soil moisture content in step 9 is as follows:

$$SMC=20.58-0.02x_1+10^{-2}x_2-1.76x_3-2\times10^{-3}x_1x_2-0.065x_1x_3-0.045x_2x_3-1.83\times10^{-4}x_1^2+7.91\times10^{-5}x_2^2+3.99x_3^2$$

$x_1$ represents chlorophyll response to soil moisture stress, $x_2$ represents wheat moisture response to soil moisture stress and $x_3$ represents soil moisture stress content.

4. The method for screening and monitoring soil moisture stress in agricultural fields based on CEEMDAN according to claim 1, characterized in that screening out soil moisture stress sequences in step 5 synthesizes the first and second IMF components $IMF_1$ and $IMF_2$ cumulatively into a soil moisture stress sequence:

$$y(n) = \sum_{n=1}^{N}(IMF_1(n) + IMF_2(n)). \qquad \text{(formula 10)}$$

5. The method for screening and monitoring soil moisture stress in agricultural fields based on CEEMDAN according to claim 1, characterized in that the chlorophyll content as a function of the amount of soil moisture stress content in step 8 described is $y1=58.241-19.917x-393.742x^2$ and the plant water content as a function of the amount of soil moisture stress content is $y2=68.121+0.404^x$, wherein x represents the amount of soil moisture stress content, y1 represents the chlorophyll content, and y2 represents the plant water content.

* * * * *